United States Patent [19]

Gunner et al.

[11] Patent Number: 5,057,316
[45] Date of Patent: * Oct. 15, 1991

[54] METHOD AND DEVICE FOR THE BIOLOGICAL CONTROL OF INSECTS

[75] Inventors: Haim B. Gunner, Amherst, Mass.; Fernando Agudelo-Silva, San Francisco, Calif.; David W. Miller, Amherst, Mass.

[73] Assignee: EcoScience Laboratories, Inc., Amherst, Mass.

[ * ] Notice: The portion of the term of this patent subsequent to Oct. 15, 2008 has been disclaimed.

[21] Appl. No.: 583,230

[22] Filed: Sep. 14, 1990

Related U.S. Application Data

[63] Continuation-in-part of Ser. No. 572,486, Aug. 23, 1990, which is a continuation-in-part of Ser. No. 324,461, Mar. 15, 1989.

[51] Int. Cl.$^5$ ............... A01N 63/00; A01N 25/00; A01M 1/00
[52] U.S. Cl. ..................... 424/93; 424/405; 424/DIG. 8; 43/132.1
[58] Field of Search ............. 424/405, 93; 43/132.1, 43/121

[56] References Cited

U.S. PATENT DOCUMENTS

| Re. 29,358 | 8/1977 | Tomcufcik | 542/417 |
|---|---|---|---|
| D. 269,290 | 6/1983 | Carlsen | D22/19 |
| D. 275,124 | 8/1984 | Carlsen | D22/19 |
| D. 278,842 | 5/1985 | Woodruff | D22/19 |
| 3,337,395 | 8/1967 | Page | 424/405 |
| 3,851,417 | 12/1974 | Wunsche | 43/121 |
| 3,908,302 | 9/1975 | Carr | 43/121 |
| 3,913,259 | 10/1975 | Nishimura et al. | 43/114 |
| 3,931,692 | 1/1976 | Hermanson | 43/131 |

(List continued on next page.)

OTHER PUBLICATIONS

Archbold et al., *Environ. Entomol,* 15(1), 221-226 (1986).
Strand and Brooks, *Pathogens of Medically Important Arthropods,* Roberts & Strand, editors *Bulletin of the World Health Organization* 55(Supp. No. 11, pp. 289-304 (Boyce Thompson Inst., Yonkers, N.Y. 10701).
Ryan and Nicholas, *J. Inveterbrate Path.,* 19, 299-307 (1972).
Appel et al., *Comp. Biochem. Physiol. A. Comp. Physiol.* 88(3) 491-494 (1987).
Verrett et al., *J. Econ. Entomol.* 80(6), 1205-1212 (1987).
Archbold et al., *J. Med. Entomol.* 24(2), 269-272 (1987).
Gunnarsson, S. G. S., *J. Invertebr. Pathol.* (46)3, 312-319 (1985).
Lin et al., *Natural Enemies of Insects* 9(3), 168-172 (1987).

Primary Examiner—John W. Rollins
Assistant Examiner—R. Gitomer
Attorney, Agent, or Firm—Kilpatrick & Cody

[57] ABSTRACT

A method for control and extermination of insects, including roaches, flying insects such as the housefly, and other insects such as the adult form of the corn rootworm by infection of the insects with a fungus that can be pathogenic when administered to the insects in a sufficiently high concentration, by means of an infection chamber. The chamber maintains the spores of a fungus pathogenic to the insects in a viable form, protecting the fungi from the environment (including rain, ultraviolet light and the wind), serves as an attractant for the insects, and serves to inoculate the insects with high numbers of spores. Although the primary means of infection is by external contact, the insects may also be infected by contact with each other and by ingestion of the spores. The two most preferred entomopathogenic fungi are *Metarhizium anisopliae* and *Beauveria bassiana,* although other fungi can be used which are pathogenic when the insect is inoculated via the infection chamber. Examples demonstrate control of *Blattella germanica* (the German cockroach), *Periplaneta americana* (the American cockroach, *Fannia canicularis* (little housefly), *Musca domestica* (housefly), and *Diabrotica undecempunctata* using chambers containing *Metarhizium anisopliae* and *Beauveria bassiana.*

8 Claims, 9 Drawing Sheets

U.S. PATENT DOCUMENTS

| | | | |
|---|---|---|---|
| 3,940,874 | 3/1976 | Katsuda | 43/114 |
| 4,030,233 | 6/1977 | Wunsche | 43/121 |
| 4,152,862 | 5/1979 | Mohiuddin | 43/121 |
| 4,173,093 | 11/1979 | Nakai | 43/121 |
| 4,208,828 | 6/1980 | Hall et al. | 43/114 |
| 4,316,344 | 2/1982 | Carlsen | 43/114 |
| 4,395,842 | 8/1983 | Margulies | 43/114 |
| 4,400,905 | 8/1983 | Brown | 43/132.1 |
| 4,411,094 | 10/1983 | Spackova et al. | 43/121 |
| 4,423,564 | 1/1984 | Davies et al. | 43/121 |
| 4,563,836 | 1/1986 | Woodruff et al. | 43/131 |
| 4,608,774 | 9/1986 | Sherman | 43/114 |
| 4,642,935 | 2/1987 | Fierer | 43/121 |
| 4,696,127 | 9/1987 | Dobbs | 43/121 |
| 4,709,502 | 12/1987 | Bierman | 43/121 |
| 4,894,947 | 1/1990 | Brandli | 43/131 |
| 4,921,703 | 5/1990 | Higuchi | 424/419 |

METHOD AND DEVICE FOR THE BIOLOGICAL CONTROL OF INSECTS

BACKGROUND OF THE INVENTION

This is a continuation-in-part of U.S. Ser. No. 07/572,486 entitled "A Method and Device for the Biological Control of Flying Insects" filed Aug. 23, 1990 by Fernando Agudelo-Silva, et al., which is a continuation-in-part of U.S. Ser. No. 07/324,461 entitled "Method and Device for the Biological Control of Cockroaches" filed Mar. 15, 1989, by Haim B. Gunner, Fernando Agudelo-Silva, and Carol A. Johnson.

The present invention is generally in the field of biological control of insect pests, specifically in the area of use of entomopathogenic fungi in an infection chamber for the control of insects.

There are many varieties of insects that cause major economic losses in agriculture and spread disease among human and other animal populations. The majority of approaches to control of these insects use pesticides. Unfortunately, pesticides are expensive and generally hazardous to the environment, particularly if effective for more than a very short term. Further, there is a tendency among the treated insects for resistant strains to develop, which requires the use of large quantities and different chemicals to treat. The use of chemical insecticides also results in the destruction of non-target biological control agents.

Insect pathogens are a possible alternative to the common use of highly toxic chemical insecticides for the control of insect pests. Fungi are one of the promising groups of insect pathogens suitable for use as biological agents for the control of insects.

Fungi are found either as single cell organisms or as multicellular colonies. While fungi are eukaryotic and therefore more highly differentiated than bacteria, they are less differentiated than higher plants. Fungi are incapable of utilizing light as an energy source and therefore restricted to a saprophytic or parasitic existence.

The most common mode of growth and reproduction for fungi is vegetative or asexual reproduction which involves sporulation followed by germination of the spores. Asexual spores, or conidia, form at the tips and along the sides of hyphae, the branching filamentous structures of multicellular colonies. In the proper environment, the conidia germinate, become enlarged and produce germ tubes. The germ tubes develop, in time, into hyphae which in turn form colonies.

The fungus *Metarhizium anisopliae* is an example of a fungus that infects certain species of insects. This fungus has been administered to insect pests by a number of methods, including direct spraying, injection, and by the application of the fungus to the plant material on which the insect lives or feeds. In some insect species, infection with the fungus has been shown to result in death. In one species, infected individuals were able to transmit the fungus to non-infected members of their colony. *Metarhizium anisopliae* is one of the most widely studied fungus for biological control of insects.

The limitation of the majority of the prior research using fungal pathogens of insects is that it has been conducted under laboratory conditions, which are quite different from the conditions under which the insects are actually found. In most reported cases, death of the treated insects has been achieved by ingestion or injection of very large quantities of spores, which may be toxic in and of themselves. In other cases, infection was achieved by rolling the insect in a test tube containing large quantities of fungal spores. It is clearly impractical to use such methods commercially. Moreover, government regulations would make it difficult to register a fungal insecticide which necessitates the random release of large quantities of fungal spores in areas of insect infestation, particularly in areas in which people or food could be contaminated. No one has yet developed a consistent and commercially viable way of infecting insects and assuring that the fungal inoculum is widely spread.

*Blattella germanica* (the German cockroach) and *Periplaneta americana* (the American cockroach) are ubiquitous throughout the world. They have been implicated as vectors of several human disease agents. There are few reports which address the ability of *M. anisopliae* to infect cockroaches. Gunnarsson, S.G.S., *J. Invertebr. Pathol.* (46)3, 312–319, (1985), for example, has shown that *Periplaneta americana* exhibits a defense reaction (nodule formation) to the injection of *M. anisopliae* conidia. Further, there are a number of insect species which are not infected by contact with entomopathogenic fungi.

Control of the house fly is of major economic importance throughout the world because of public health concerns. The fly has the potential to mechanically transmit a wide variety of human pathogens, as reviewed by Bida Wid, S.P., J. I. Braim and R.M. Matossian, *Ann. Trop. Med. Parasitol.* 72(2): 117–121 (1978). The fly can also be annoying to people, livestock and poultry, to the extent that it even decreases time spent by animals in feeding, thereby decreasing feed efficiency.

A review of the literature reveals the scarcity of pathogens that appear to offer potential to control *M. domestica*. The bulk of scientific literature on associations of pathogens with house flies refers to isolated reports of diagnosis of dead flies or laboratory studies without practical, short-term applications. Most fungal infections of flies appear to be innocuous, as demonstrated by the isolation of the fungi *Aspergillus niger, A. flavus, A. ustus* and *Mucor racemosus* from pupae or adults of *M. domestica* by Zuberi, et al., *Pakistan J. Sci. Ind. Res.* 12, 77–82 (1969). There was no evidence of significant effect on the fly populations.

It is possible to infect adult house flies with fungi under certain laboratory conditions, leading to death of the infected flies. For example, *Aspergillus flavus* was pathogenic to *M. domestica* when the insects were fed high concentrations (up to $1 \times 10^9$) of fungal spores, presumably due to toxins in the spores. Mortality after seven days of exposure was 57%; mortality was 100% twenty-one days after exposure. One hundred percent mortality occurred in flies seven days after they were anesthetized and placed in contact with fungal spores, as reported by Amonker and Nair, *J. Invertebr. Pathol.* 7: 513–514 (1965). Dresner, *J. N.Y. Entomol. Soc.* 58: 269–279 (1950), also reported that an isolate of the fungus *Beauveria bassiana* infected adult *M. domestica* when the insects were exposed to a dust of germinating conidia adhered in a nutrient medium. The fungus was also infective to flies when the insects were exposed to a dish of milk containing fungal conidia.

D. C. Rizzo conducted studies, reported in *J. Invert. Pathol.* 30, 127–130 (1977), on the mortality of flies infected with either *Metarhizium anisopliae* or *Beauveria*

*bassiana* and determined that the time to death after infection was independent of age. Flies were infected by rolling them for ten minutes in four-week-old fungal culture slants until they were completely exposed to the spores, then maintaining them in humidity chambers. As noted by the author, in reference to the infecting fungi, "these pathogens have never been reported as having caused mycoses in fly populations in nature" at page 127.

In 1990, however, D.C. Steinkraus, et al., reported in *J. Med. Entomology* 27(3), 309–312, that *Musca domestica L.*, infected with *Beauveria bassiana* had been found on dairy farms in New York, although at a prevalence of less than 1% (28 out of 31,165). Isolates of the fungi were infective for laboratory raised flies, but the low naturally occurring incidence led to the conclusion by the authors that "it seems unlikely that these infections represent naturally occurring epizootics within house fly populations" Id. at page 310.

These studies have led to the recognition that there is a potential for fungal control of insects. However, no one has yet developed a consistent and commercially viable way of infecting insects and assuring that the fungi are dispersed throughout the breeding populations for the management and biological control of insects infesting houses or buildings.

It is therefore an object of the present invention to biologically control insects using entomopathogenic fungi.

It is a further object of the present invention to provide a device for the convenient, reliable and economically feasible application of fungi in the biological control of insects.

It is a further object of the present invention to provide a method and means for infecting all insects in a breeding colony by dissemination of a fungi pathogenic for insects.

It is another object of the present invention to provide a method and means for infection and killing of insects by a variety of fungi so that development of resistant strains is avoided.

SUMMARY OF THE INVENTION

A method for control and extermination of insects, including roaches, flying insects such as the housefly, and other insects such as the adult form of the corn rootworm by infection of the insects with a fungus that can be pathogenic when administered to the insects in a sufficiently high concentration, by means of an infection chamber. The chamber maintains the spores of a fungus pathogenic to the insects in a viable form, protecting the fungi from the environment (including rain, ultraviolet light and the wind), serves as, or houses, an attractant for the insects, and serves to inoculate the insects with high numbers of spores. The fungal culture provides a continuous supply of spores over a prolonged period of time. The spores attach to the insects and originate germ tubes that penetrate into the insect, which can result in death within three to four days. The chamber design, i.e., shape and color, can be the sole attractants for the insects. Alternatively, food or scents can be used to further enhance the attraction of the insects for the chamber. Although the primary means of infection is by external contact, the insects may also be infected by contact with each other and by ingestion of the spores. In some case, the ingested fungal conidia can also be toxic.

The two most preferred entomopathogenic fungi are *Metarhizium anisopliae* and *Beauveria bassiana*, although other fungi can be used which are pathogenic when the insect is inoculated via the infection chamber. Examples demonstrate control of *Blattella germanica* (the German cockroach), *Periplaneta americana* (the American cockroach), *Fannia canicularis* (little housefly), *Musca domestica* (housefly), and *Diabrotica undecempunctata* using chambers containing *Metarhizium anisopliae* and *Beauveria bassiana*.

BRIEF DESCRIPTION OF THE DRAWINGS

FIG. 8 is a perspective view of an infection chamber for infection of flies by entomopathogenic fungi, consisting of a housing, culture medium, sporulating fungal culture, and attractant.

DETAILED DESCRIPTION OF THE INVENTION

Figure 1:
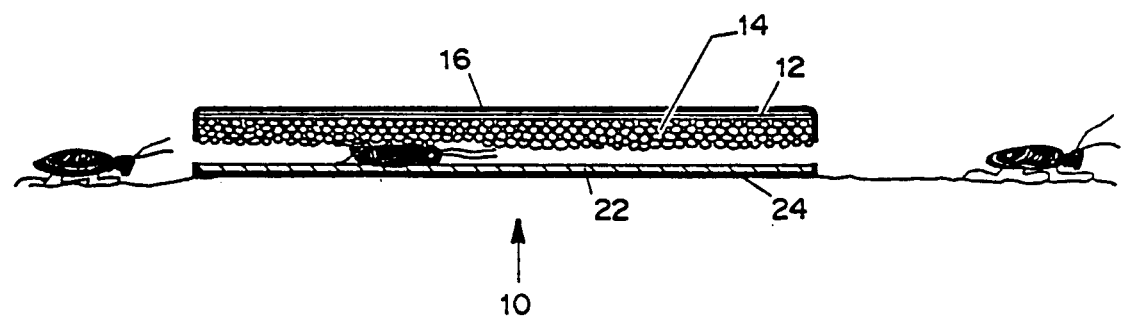
FIG. 1 is a cross-sectional view of an infection chamber for infection of roaches by entomopathogenic fungi, consisting of a culture of fungus deposited as a mat on a nutrient-containing agar ceiling and a floor with a sterile polystyrene pad to maintain the humidity within the chamber. The two opposing surfaces are separated by a space of 2 to 3 mm through which the cockroach travels.

The methods and devices described below provide a convenient and reliable method for the administration of entomopathogenic fungi, relatively non-toxic to animals other than insects, in an economical and cost-effective fashion. The small, lightweight infection chambers are unobtrusive and are easily placed in locations of heavy insect infestation, increasing the efficacy of the device. Because the devices provide an environment within which the fungus can flourish over extended periods of time, a single device is effective for a longer period of time than with other methods, such as spraying, where effectiveness of the agent dissipates over a short time. The longevity of the inoculum in the devices decreases the frequency and total number of applications required for effective treatment. Another advantage of the devices is that they are constructed of readily available and relatively inexpensive materials, which insures an abundant supply of cost-effective devices.

The Infection Chambers

The primary advantages of the infection chamber are that (1) it concentrates an extremely high number of fungal inoculum in a very small space within the infection chamber, forcing entering insects into contact with the spores which infect and kill the insects, and (2) it contains the fungal spores, resulting in minimal exposure of the environment to the pathogenic fungi, and protecting the fungus from the environment, thereby increasing viability of the culture and minimizing contamination of the fungal culture. Because the devices provide an environment within which the fungus can flourish over extended periods of time, a single device is effective for a longer period of time than with other methods, such as spraying, where effectiveness of the agent dissipates over a short time. The longevity of the devices also decreases the number of applications and maintenance time required for effective treatment. Another advantage of the devices is that they are constructed of readily available and relatively inexpensive materials, which insures an abundant supply of cost-effective devices.

In a preferred embodiment, the insects are infected by exposure to the fungus in small chambers having apertures through which the insects enter and exit. An insect enters the chamber either as the result of general exploration or as the result of being lured inside the device by the action of an attractants (such as food sources or pheremones). Once inside the chamber the insect comes in contact with the entomopathogenic fungus. The conidia of the fungus attach to the body of the insect. After attachment, the conidia germinate on the integument and the germ tubes of the germinating conidia penetrate the cuticle of the insect. The germ tubes continue to penetrate through the cuticle of the insect until they reach the internal body cavity (hemocoel) of the insect, thereby killing the insect. After the insect dies, given the appropriate conditions of relative humidity and temperature, the fungal mycelia may sporulate on the body of the insect, and other insects may be infected by exposure to the conidia produced on the dead insect. Exposure of other insects to the spores on the surface of infected insects, or the body of the infected insect after the fungus has sporulated on the dead body of the infected insect effectively transmits the pathogen via the infected insect to other non-infected insects. Some insects may also ingest the spores, which can thereby contribute to, or cause, death of the insect.

Selection of the Fungus

At least two strains of each of two species of entomopathogenic fungi, *Metarhizium anisopliae* and *Beauveria bassiana,* have been shown to be effective in control of roaches, flies, and the adult corn rootworm. Others that should be useful are fungi that are easy to grow on artificial media and quickly grow and produce large amounts of conidia. Examples include *Verticillium* and *Paecilomyces* spp. Useful fungi can be obtained as isolates from infected insects or from the American Type Culture Collection, 12301 Parklawn Drive, Rockville, Md. 20852, USA, where they are available without restriction.

Culture Media for Fungus

Suitable culture media are known which can be used in the chamber. Examples of media known to those skilled in the art and which are commercially available include potato, dextrose, agar, or rice agar.

An example of a useful culture medium for Metarhizium and Beauveria consists of 1% dextrose, 1% yeast extract, 5% rice flour, 1.5% agar and 0.5% 5x Dubois sporulation salts. The 5x Dubois sporulation salts consists of 15 g $(NH_4)_2SO_4$ /1,000 ml; 0.30 g $MgSO_4$ $7H_2O$/1,000 ml; 0.15 g $MnSO_4$ $H_2O$/1,000 ml; 0.0375 g $CuSO_4$ $5H_2O$/1,000 ml; 0.0375 g $ZnSO_4$ $7H_2$/1,000 ml; and 0.0038 g $FeSO_4$ $7H_2O$;/1,000 ml. Each salt is completely dissolved before the next salt is added and the solution is autoclaved. Other useful culture mediums are known, or can be optimized from those that are known, by those skilled in the art.

Inoculation of the Medium with Fungal Spores

Figure 2:
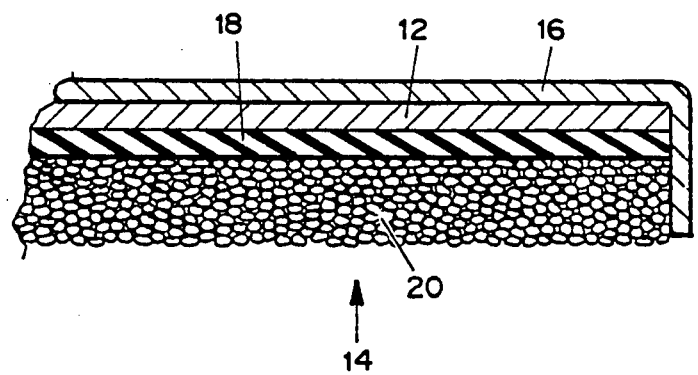
FIG. 2 is an enlarged cross-sectional view of the chamber of FIG. 1 containing 50 ml of fungal culture media and inoculated with an entomopathogenic fungus which has formed a mat of hyphae and conidia (spores).
Figure 3:
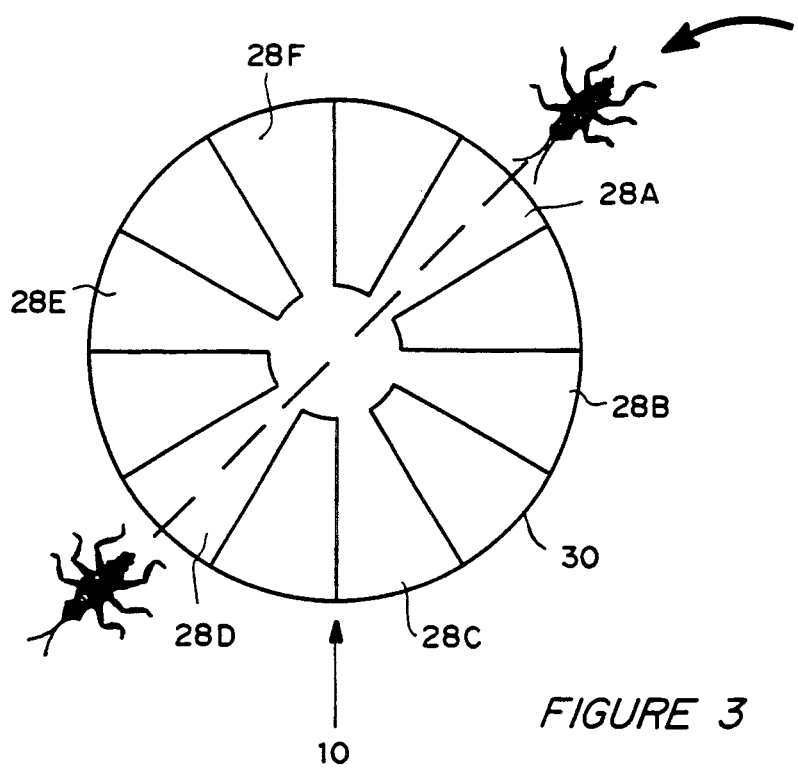
FIG. 3 is a cross-sectional view of the top of the chamber of FIG. 1 showing the openings spaced equidistantly around the perimeter.
Figure 4:
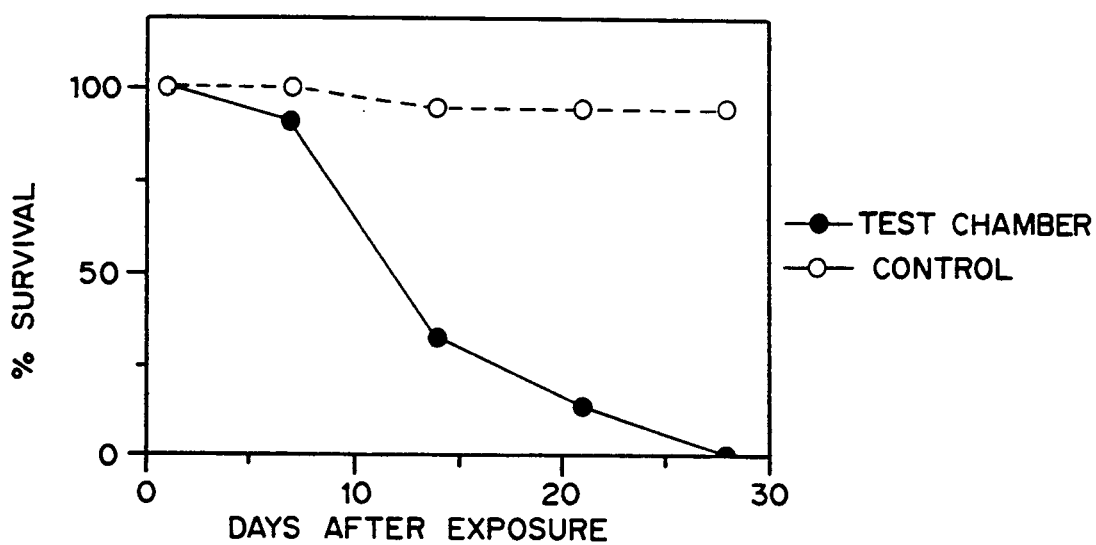
FIG. 4 is a graph of mortality of adult *Blatella germanica* cockroaches (% survival) as a function of time after exposure (days) to *M. anisopliae* infection chambers, at a temperature of 28° C. and humidity of 75% (control, --O--; exposed, --dark circle--).

As diagrammed in FIG. 1, an infection chamber 10 suitable for infecting cockroaches can be constructed by pouring 50 ml of culture medium 12 for the fungus 14 into a dish 16, for example, a 100×15 mm plastic petri dish. The culture medium is inoculated with spores of the appropriate fungal pathogen (inoculation is accomplished by streaking the surface of the medium with an inoculating loop carrying fungal spores or by mixing the spores with the liquid medium). As shown in FIG. 2, after seven days of growth at 28° C. with 75% relative humidity, the fungus 14 will have produced a thick layer of mycelia 18 and conidia 20 that cover the surface of the culture medium 12. The dish 16 is then inverted so that the culture medium 12 with the fungal growth 14 is now the ceiling of the chamber 10.

Chamber Design.

The chamber can be constructed using conventional materials, including glass or metal, but is preferably constructed of an extrudable or moldable plastic to keep costs to a minimum. The chamber must have openings large enough to allow free passage of the insects. The top of the chamber preferably fits securely over the bottom, or the chamber is constructed of one piece. The location of food attractants and landing platform, if any, should be such that the insects are forced into close contact with the spores. The chamber can be designed so that the fungus grows on the bottom, top and/or sides of the chamber, to maximize infectivity. The insects are infected when they contact the fungus in the chamber, or when during grooming from spores acquired on their legs.

As shown in FIG. 1, a sterile polystyrene pad 22 is placed in the bottom 24 of the chamber 10. The inverted chamber 10 has a 2 to 3 mm space between the surface of the sporulated fungus 26 on the ceiling of the chamber and the polystyrene floor 22 of the chamber. As depicted in FIG. 1, this forces the roaches to come in contact with the fungus as they pass through the chamber 10.

The chamber 10 is shown in cross-section in FIG. 3. Openings 28*a*–28*f* are made on the perimeter 30 of the chamber 10, each opening being 9 mm square and equidistantly spaced around the perimeter of the infection chamber. The size of the openings is proportional to the size of the insect. For example, larger openings are used for control of large species of cockroaches, such as the Oriental cockroach. When the chambers are placed in habitats infested with cockroaches, the latter enter the chamber through the openings, where they are forced into contact with the fungal spores.

Insects that can be infected using the Fungal Infection Chambers

The infection chambers containing a fungus that can be a pathogen, if administered to the insect in an effective amount, are useful against a variety of insects that are attracted to, or otherwise encouraged to pass through, the chambers. Examples below demonstrate efficacy against two species of cockroach, two species of flies, and the adult form of the corn rootworm, a type of beetle. Although described with reference to flies, especially the common housefly *M. domestica,* the term "flies" is used to refer to any type of flying insect which will enter the device and be infected by the entomopathogenic fungi. Examples of flying insects include other flies such as the little housefly (*Fannia canicularis*), tsetse fly, Mediterranean fruit fly, and Oriental fruit fly, wasps, white flies, and the adult forms of some insects, such as the corn rootworm, *Diabrotica undecemounctata.*

Attractants

Attractants that are useful will be dependent on the type of insect to be controlled. For example, attractants for flies include fruit, such as raisins, pheromones such as the sex pheromone muscalure, described by Carlson and Bereza *Environ. Entomol.* 2, 555–560 (1973), and synthetic compounds, such as the feeding attractant Lursect TM, McClaughlin, Gormley and King Co., Minneapolis, Minn. The shape and/or color of the chamber, as well as the location of the chamber, can also be used to attract flying insects. Three studies conducted on the spatial and temporal responses of flies to attractive bait, and the attractiveness and formulation of different baits, are reported by Willson and Mulla, in *Environ. Entomol.* 4(3), 395–399 (1975) and 2(5), 815–822 (1973) for *Musca domestica* and by Mulla, et al., *Environ. Entomol.* 66(5), 1,089–1,094 (1973).

The following non-limiting examples demonstrate the efficacy of the infection chambers in controlling three distinct orders of insects. In all cases the insect populations were significantly reduced by the fungus present in the infection chambers.

EXAMPLE 1

Infection and Death of *Blattella germanica* at different stages of development with Metarhizium anisopliae Strain PA-2

The study utilized a plastic container in the shape of a box (6×12×4 in) to hold the cockroaches. The lid had ten circular ventilation holes (⅜ inch diameter). The holes were screened with insect netting to prevent the escape of insects and the accumulation of moisture. Three different stages of *Blattella germanica* (German cockroach) development were studied: immature cockroaches at the third instar stage, immature cockroaches at the sixth instar stage, and adult insects. Twenty insects, 10 males and 10 females of each developmental stage, were studied per box. Each developmental stage was studied in duplicate. Controls, exposed to infection chambers without fungus, were utilized to determine normal cockroach mortality for each stage.

One infection chamber was placed in one end of each box. The chamber was placed in such a manner that the fungus was on the ceiling of the chamber. The side apertures of the chamber were open so that the cockroaches could enter the device. Food, Purina ® lab chow, and water for the roaches were placed on the other end of the box.

When the cockroaches entered the infection chamber, the conidia of the fungus attached to the roaches, the conidia germinated and invaded the body of the cockroach, and the roaches died.

The mortality of the roaches was tallied every week for six weeks. The results of this and other similar studies are presented in FIGS. 4 and 5 and in Table 1 and clearly demonstrate the efficacy of the devices for all of the developmental stages of the German cockroach.

TABLE 1

% Death of Roaches infected with *M. anisopliae*. Strain PA-2

| Weeks After Exposing the Roaches to the Infection Chamber | Percent Cockroach Survival Developmental Stage | | |
|---|---|---|---|
| | Third | Sixth | Adult |
| 2 | 85 | 95 | 80 |
| 3 | 80 | 60 | 60 |
| 4 | 60 | 45 | 45 |
| 6 | 15 | 10 | 5 |

Survival of the control population of cockroaches was greater than 90 percent. This strain of fungus, *Metarhizium anisopliae* Strain PA-2, was originally selected by exposing cockroaches to *Metarhizium anisopliae*, isolating the fungus from dead cockroaches and culturing the fungus in artificial culture medium.

EXAMPLE 2

Long Term Killing of Roaches by Infection Chambers

This study demonstrates that the devices of the present invention are effective in maintaining an active entomopathogenic fungal culture over a long period of time and that the fungal spores in the infection chamber remain infective to cockroaches for many weeks. From a practical perspective, the importance of this study is that it demonstrates that the chambers may be useful over a commercially acceptable period.

As in the preceding study, infection chambers were placed in plastic boxes containing cockroaches at different developmental stages. At the third week and sixth week, the infection chambers were transferred to fresh boxes containing 20 different (uninfected) German cockroaches of the corresponding developmental stage. Cockroach mortality in each box in which a chamber was placed was tallied at weekly intervals for six weeks. The results of this study appear in Table 2.

TABLE 2

Effective Lifetime of Infection Chambers.

| Age of Chamber Weeks | Weeks After Exposure to Chamber | % Cockroach Survival Instar Exposed | | |
|---|---|---|---|---|
| | | III | VI | Adults |
| 0 | 2 | 95 | 90 | 98 |
| | 3 | 80 | 23 | 73 |
| | 4 | 60 | 10 | 50 |
| | 6 | 58 | 10 | 3 |
| 3 | 2 | 95 | 80 | 83 |
| | 3 | 90 | 30 | 58 |
| | 4 | 85 | 18 | 40 |
| | 6 | 58 | 3 | 18 |
| 6 | 2 | 88 | 65 | 55 |
| | 3 | 88 | 45 | 45 |
| | 4 | 60 | 10 | 10 |
| | 6 | 13 | 5 | 0 |

Figure 5:
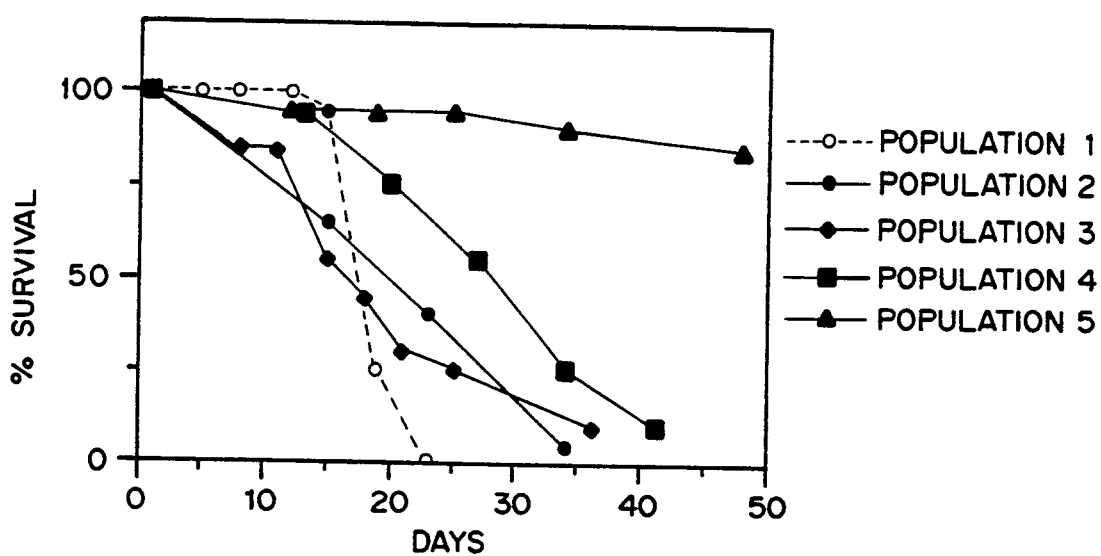
FIG. 5 is a graph of mortality of five populations of adult *Blatella germanica* cockroaches (% survival) as a function of time after exposure (days) to a single *M. anisopliae* infection chamber, at a temperature of 28° C. and humidity of 75%, where each population of roaches was exposed to the chamber for three weeks.

As it can be concluded from this study, the effectiveness of the infection chamber in reducing roach populations was the same when the chambers were freshly made (age 0 weeks) as when the chambers were three to six weeks old. For example, sixth instar roaches, after being exposed to six week old chambers, exhibited essentially the same percent survival as roaches exposed to new chambers (0 weeks old). These results establish that the chambers maintain their killing power for greater than six weeks, indicating that the chambers may be used to significantly reduce roach populations for at least six weeks. A variation of this study demonstrated the same results. Five populations were consecutively exposed to a single infection chamber containing *M. anisopliae* ATCC 62176 for three weeks. The results, shown in FIG. 5, demonstrate that the infection chamber is highly effective, even up to fifteen weeks.

The survival of control cockroaches in all cases was greater than 90 percent.

EXAMPLE 3

Effectiveness of the Addition of a Roach Attractant to the Infection Chamber

This study was to ascertain whether the effectiveness of the infection chamber killing cockroaches could be improved by introducing a cockroach attractant into the chamber. Two attractants were tested, banana extract and Purina ® laboratory chow. The attractants were placed on the floor of the infection chamber.

Figure 6:
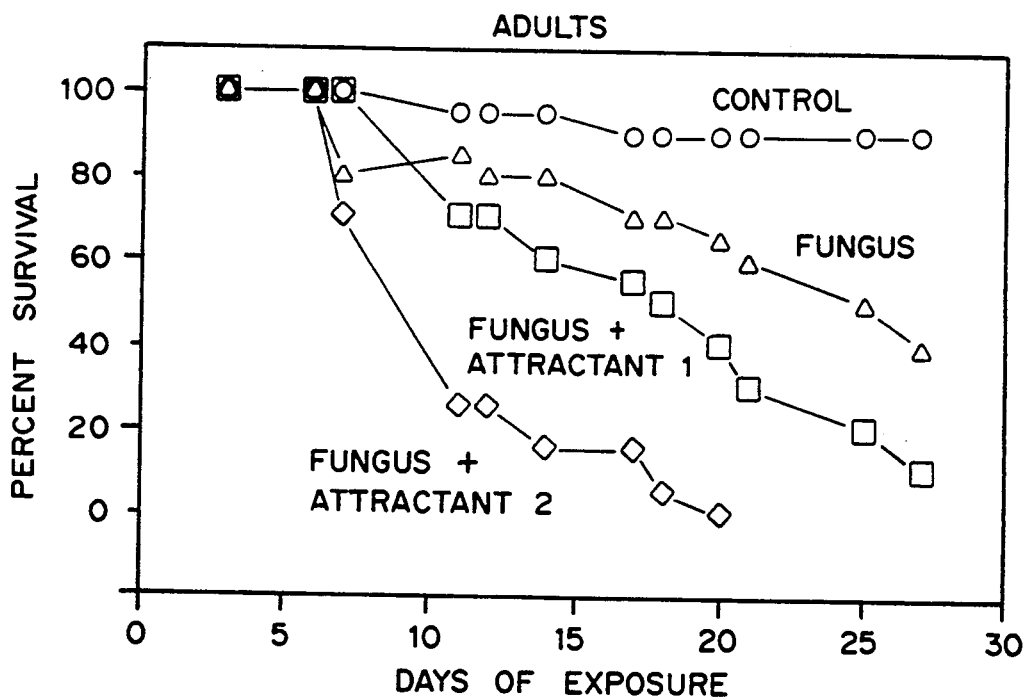
FIG. 6 is a graph of the mortality of cockroaches (% survival) as a function of time after exposure (days). Studies of cockroach mortality were conducted without pathogenic fungus (-O--O-), with the entomopathogenic fungus *M. anisopliae* but without attractant (triangles), with *M. anisopliae* and the attractants (1) banana extract (squares), and with *M. anisopliae* and (2) Purina ® lab chow (diamonds).

The methodology followed for this study is as outlined in Examples 1 and 2, with results shown for adult German cockroaches in FIG. 6. The results establish that the addition of a cockroach attractant to infection chambers appears to increase cockroach mortality relative to chambers to which no attractant had been added.

EXAMPLE 4

Infection and Death of *Periplaneta americana* with *Metarhizium anisopliae* Strain PA-2

The methodology for this study is similar to that utilized for the studies of examples 1, 2, and 3, except that *Periplaneta americana* (American cockroach) were used as the test insects and moist sponges were placed in the boxes to provide a higher relative humidity, enhancing the activity of the fungus on the cockroaches.

The results are shown in Table 3.

TABLE 3

Effect of *M. anisopliae* strain PA-2 infection on survival of *Periplaneta americana*.

| Weeks After Exposing the Cockroaches to the Chamber | Percent Cockroach Survival (%) |
|---|---|
| 1 | 70 |
| 2 | 25 |
| 3 | 15 |

The survival of control roaches was greater than 90 percent.

The preceding studies demonstrated that, using the appropriate device, cockroaches can be infected with a selected strain of *M. anisopliae*. The following studies demonstrate that other entomopathogenic fungi can be used in the infection chamber to kill cockroaches.

EXAMPLE 5

Infection and Death of *Blattella germanica* (German cockroach) with another *M. anisopliae* strain and *Beauveria bassiana*

This study utilized different potential pathogenic fungi, *Beauveria bassiana* and *Paecilomyces farinosus* strain 38 F-6, as well as a second strain of *M. anisopliae*, in the infection chambers. Other details of this study are as described above for Example 1, using German cockroaches.

As established by the results shown in Table 4 and Table 5, *Beauveria bassiana*, as well as at least one other strain of *M. anisopliae*, are effective at infecting and killing both German and American cockroaches at the sixth instar and adult stages. However, at least one other strain of fungus, *Paecilomyces farinosus* strain 38 F-6, was not pathogenic for roaches under these conditions.

TABLE 4

Infection and Death of *Blattella germanica* (German cockroach) with *M. anisopliae* strain PA-2, *M. anisopliae* strain 1958, *Beauveria bassiana* strain 252 F-9, and *Paecilomyces farinosus* strain 38 F-6.

| Days After Exposing Cockroaches to the Chamber | Percent Cockroach Survival (VI-Instar) | | | | | |
|---|---|---|---|---|---|---|
| | | Fungal Strain | | | | |
| | Control | Ma PA-2 | Ma RS-703 | Ma 1958 | Bb 252 F-9 | Pf 38 F-6 |
| 1 | 100 | 100 | 100 | 100 | 100 | 100 |
| 4 | 100 | 100 | 100 | 100 | 100 | 100 |
| 13 | 95 | 90 | 75 | 75 | 80 | 90 |
| 20 | 95 | 40 | 65 | 40 | 75 | 90 |
| 26 | 95 | 25 | 50 | 25 | 45 | 90 |
| 29 | 95 | 50 | 15 | 15 | 40 | 85 |

Ma PA-2: *M. anisopliae* strain PA-2
Ma RS-703: *M. anisopliae* strain RS-703
Ma 1958: *M. anisopliae* strain 1958
Bb 252 F-9: *Beauveria bassiana* strain 252 F-9
Pf 38 F-6: *Paecilomyces farinosus* strain 38 F-6

From this study, it is clear that Ma Pa-2, Ma RS-703, Ma 1958 and Bb 252 F-9 significantly reduced cockroach survival when cockroaches are infected at the sixth instar stage. It is equally clear that another entomopathogenic fungus, *P. farinosus,* was not effective in killing significant numbers of immature roaches.

Some of the isolates that were found to be infective to sixth instar cockroaches were also infective against adult cockroaches, as shown in Table 5.

TABLE 5

Infection and Death of *Blattella germanica* (German cockroach) with *M. anisopliae* strain PA-2, *M. anisopliae* strain 1958, *Beauveria bassiana* strain 252 F-9, and *Paecilomyces farinosus* strain 38 F-6.

| Days After Exposing Cockroaches to the Chamber | Percent Cockroach Survival (Adults) | | | | | | |
|---|---|---|---|---|---|---|---|
| | | Fungal Strain | | | | | |
| | Control | Ma PA-2 | Ma RS-703 | Ma 1958 | Bb 252 F-9 | Bb 533-10 | Pf 38F-6 |
| 1 | 100 | 100 | 100 | 100 | 100 | 100 | 100 |
| 4 | 100 | 100 | 100 | 100 | 100 | 100 | 100 |
| 13 | 100 | 100 | 100 | 100 | 95 | 95 | 100 |
| 20 | 100 | 90 | 100 | 85 | 95 | 100 | 95 |
| 26 | 100 | 45 | 100 | 35 | 65 | 100 | 90 |
| 29 | 100 | 30 | 90 | 30 | 60 | 100 | 90 |

It can be concluded that Ma PA-2, Ma 1958 and Bb 252 F-9 reduce survival of adult cockroaches.

Other strains of virulent fungi can be isolated by screening fungi for their response to various elements on the cockroach cuticle, such as soluble substances that enhance attachment and conidia germination. This selective screening provides a method for developing useful pathogen/host systems, thereby increasing the number of fungi that can be used for roach control int eh infection chamber.

EXAMPLE 6

Figure 7A:
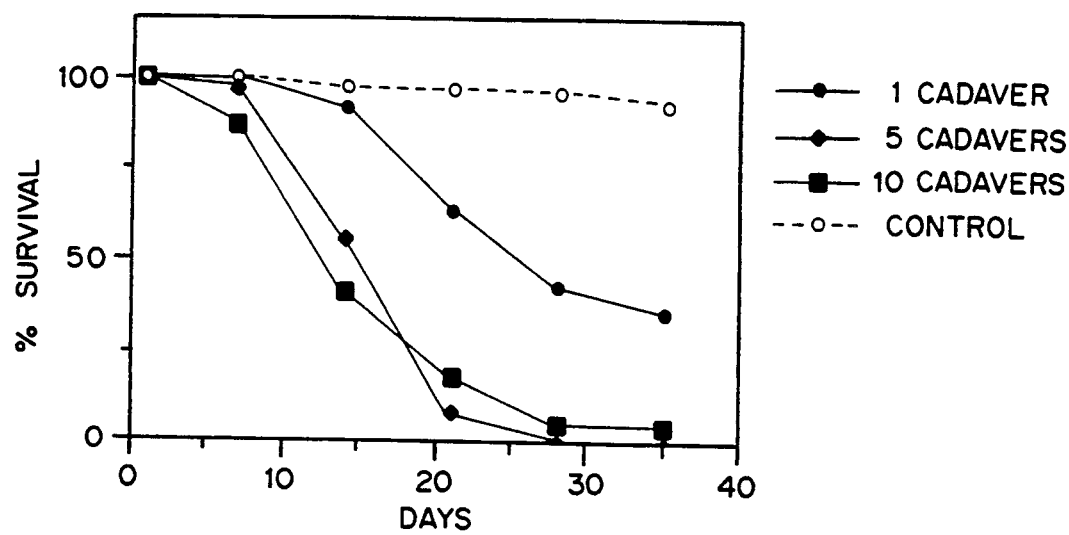
FIGS. 7A and 7B are graphs of the mortality of cockroaches (% survival) as a function of time (days post exposure to fungus) exposed to sporulating cadavers (FIG. 7A, control (- - open square - -), one cadaver (--dark hexagon--), five cadavers (--dark triangle--), and ten cadavers (--dark square--), infected with *M. anisopliae*) or contaminated individuals (FIG. 7B, comparing uninfected (--dark square--), infected (--open square--), control (- - dark square - -), and control (- - open square - -)), at 28° C. and 75% humidity.
Figure 7B:
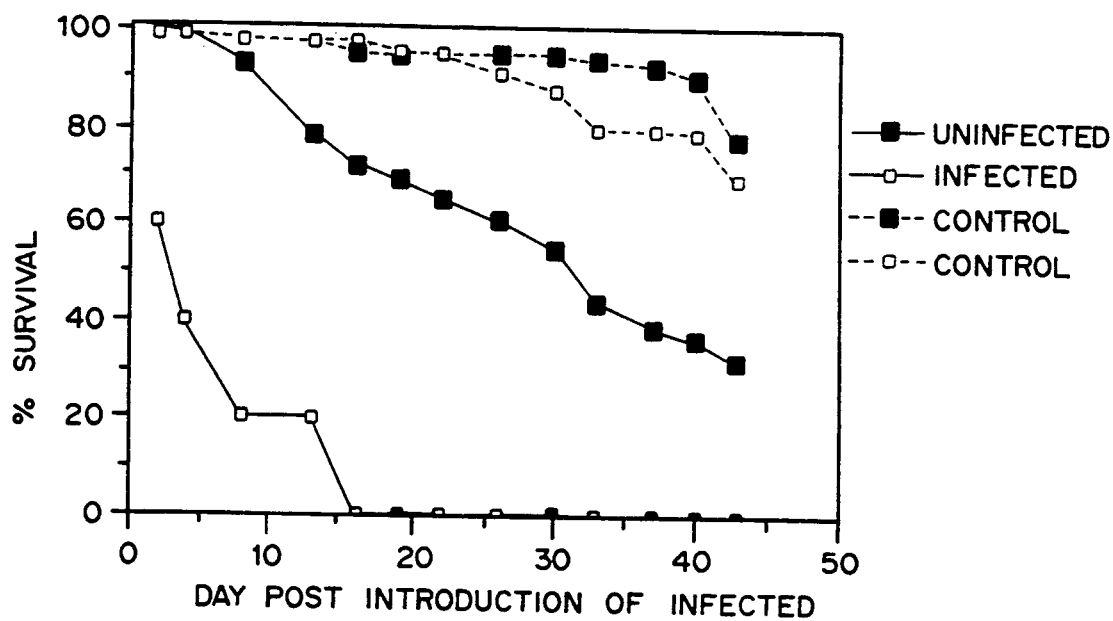

Infection of *Blatella germanica* by contact with sporulating cadavers and exposure to infected individuals Twenty uninfected roaches were placed in a box with 1, 5, or 10 sporulating roach cadavers and an infection chamber containing *M. anisopliae* added to the box to assess the infectivity of the cadavers. Mortality was assessed weekly. Ten roaches that had entered an infection chamber were placed in a box with twenty uninfected roaches and mortality assessed twice weekly (in quadruplicate) to assess the infectivity of exposed, living roaches. The results are shown in FIGS. 7A and 7B, for mortality by contact with sproulating cadavers and mortality from exposure to infected individuals, respectively.

The study conclusively demonstrates that both the exposed, living roaches, and the sporulating cadavers are highly infective for healthy roaches.

EXAMPLE 7

Infection of *Musca domestica* with Fungi in Infection Chambers

Figure 8A:
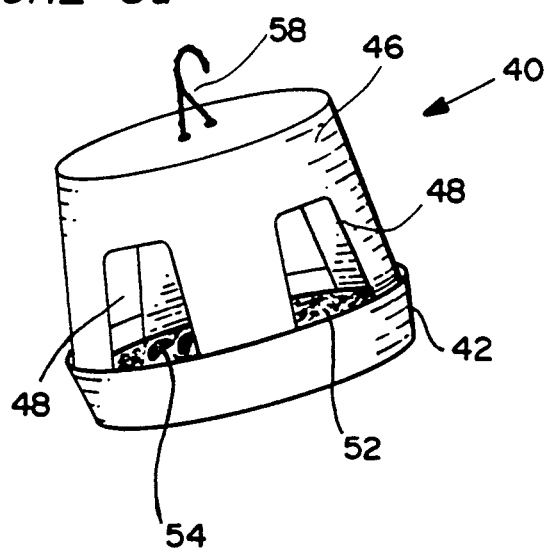
FIG. 8A is viewed from the exterior of the chamber.
Figure 8B:
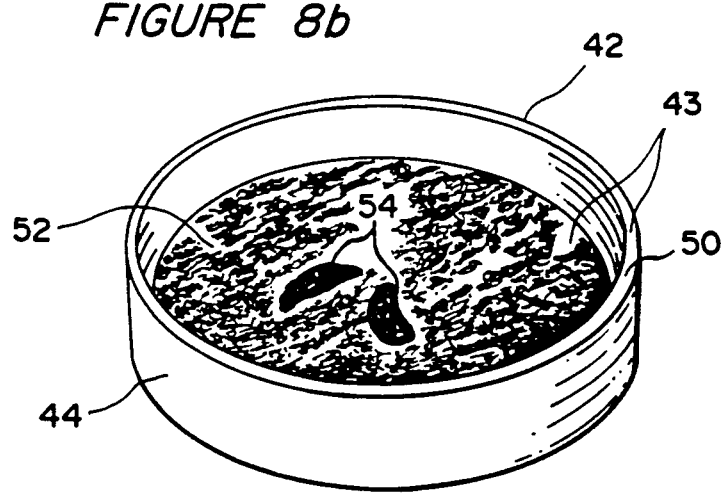
FIG. 8B is a view of the interior bottom portion of the chamber.

As diagrammed in FIG. 8A and 8B, an infection chamber 40 can be constructed using standard technology to form a container 42 for fungal culture medium 44 and a cover 46 for the chamber, having openings 48 allowing insects free access to the interior of the chamber. The fungus grows on the medium 44, forming mycelia 50 and spores 52. A food attractant 54 is located on the interior of the chamber 40, in close proximity to the spores 52. The attractant is optionally located on a platform secured to the container 42 or the cover 46 to avoid direct contact with the fungus, which can serve as a landing platform for the flies. Moisture content can be regulated by the design of the chamber, for example, by the size and number of openings. In the preferred embodiment, the chamber is hung via a hook 58 in a location most likely to attract flying insects.

These infection chambers were used in the following studies. House fly pupae were placed in closed cages that had either a infection chamber with sporulating fungus (treatment chamber) or a control chamber without fungus. Vials containing sugar, powdered milk, water, and cotton were provided in each cage to assure that the adult flies had an energy source and water when they emerged from the pupae.

After the adult flies emerged, mortality was recorded daily and plotted. Selected dead flies from the treatment chamber were surface-sterilized, examined under the microscope and found to be infected, and incubated in wet chambers to ascertain whether the entomopathogenic fungus that was in the treatment cultures would grow from the dead flies.

Figure 9:
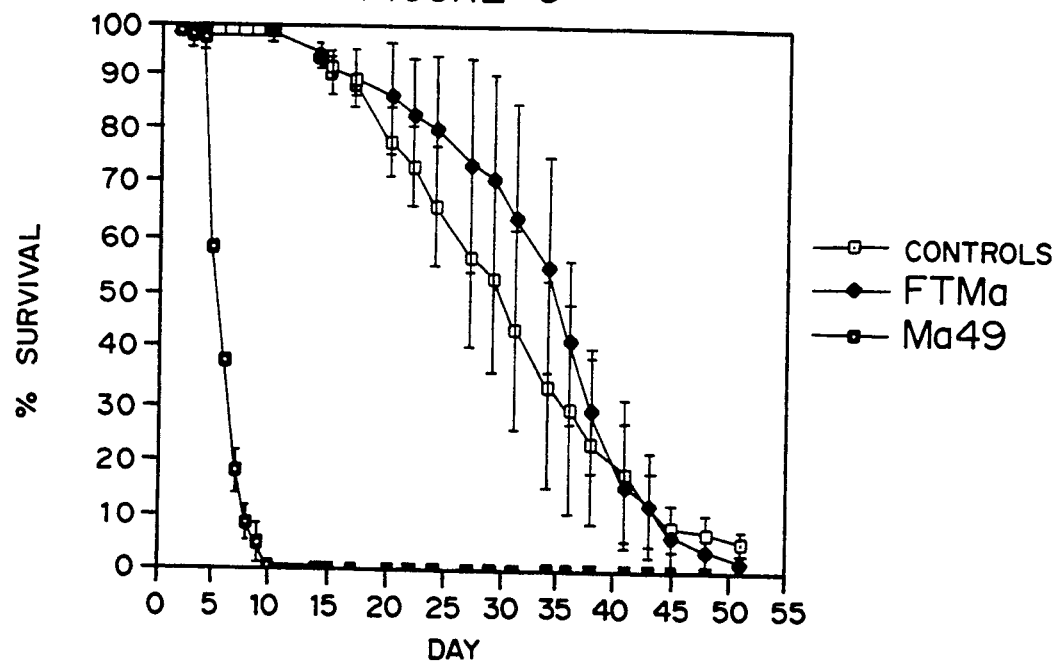
FIG. 9 is a graph of the mortality of *M. domestica* (% survival) as a function of time after exposure (days) to a chamber containing *Metarhizium anisopliae* (empty squares); formaldehyde treated fungus (diamonds) or chamber without fungus (dotted squares).
Figure 10:
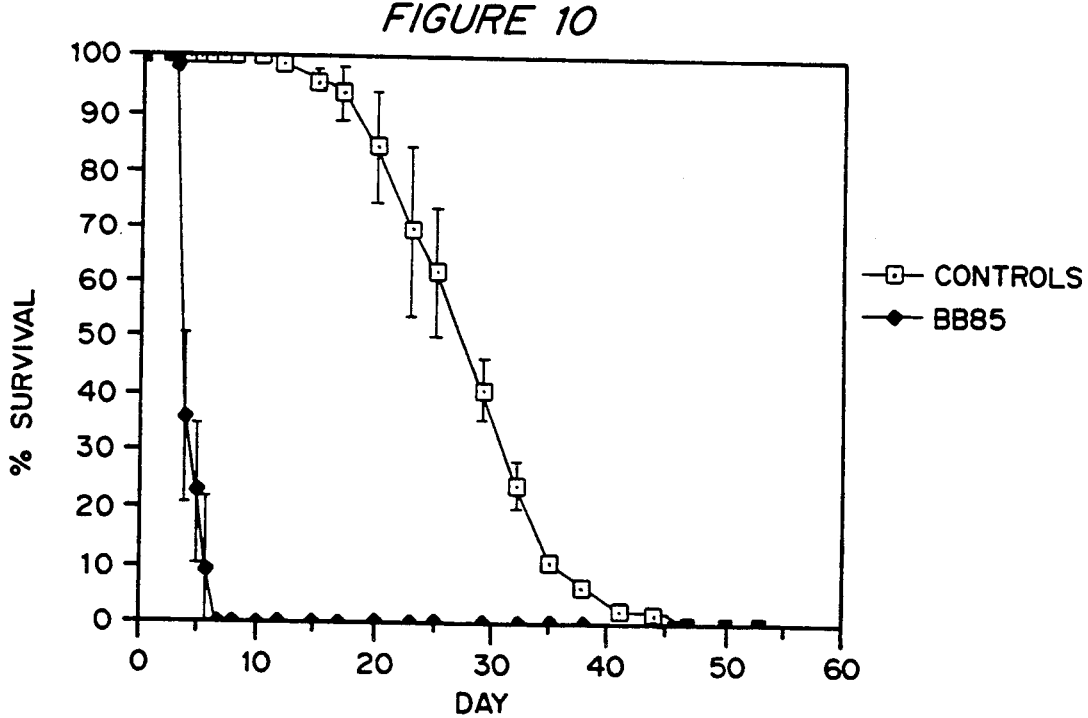
FIG. 10 is a graph of the mortality of *M. domestica* (% survival) as a function of time after exposure (days) to a chamber containing *Beauveria bassiana* (diamonds) or chamber without fungus (dotted squares).

Exposure of the adult flies to the chambers containing either the fungi *Metarhizium anisopliae* or *Beauveria bassiana* resulted in a significant reduction in survival of adult house flies as compared to flies exposed to chambers without fungus, as shown by FIGS. 9 and 10, respectively. FIG. 9 summarizes the results of the study where flies were exposed to *M. anisopliae*. 80% of the flies were dead after only five days; almost 100% were dead by seven days following exposure to the fungus. Formaldehyde-killed fungus did not results in a greater mortality than controls exposed to the chambers without fungus. FIG. 10 summarizes the results of the study where flies were exposed to *B. bassiana*. Essentially 100% of the flies were dead by four days following exposure to the fungus.

Dead surface-sterilized flies from the treatment chambers that were exposed to *B. bassiana* were examined and found to contain fungus inside of the bodies. This demonstrates that the fungus infected the flies and invaded the flies internally before they died.

EXAMPLE 8

Infection of *Fannia canicularis* with Fungi in Infection Chambers

Fly pupae were placed in closed cages. One week after emergence either a fly chamber with sporulating fungus (treatment chamber) or a control chamber without fungus were added to the cage. Vials containing sugar, powdered milk, water and cotton, were provided in each cage to assure that the adult flies had an energy source and water when they emerged from the pupae. Fungi were obtained from the American Type Culture Collection, 12301 Parklawn Drive, Rockville, Md. 20852, USA, where they are available without restriction.

Figure 11:
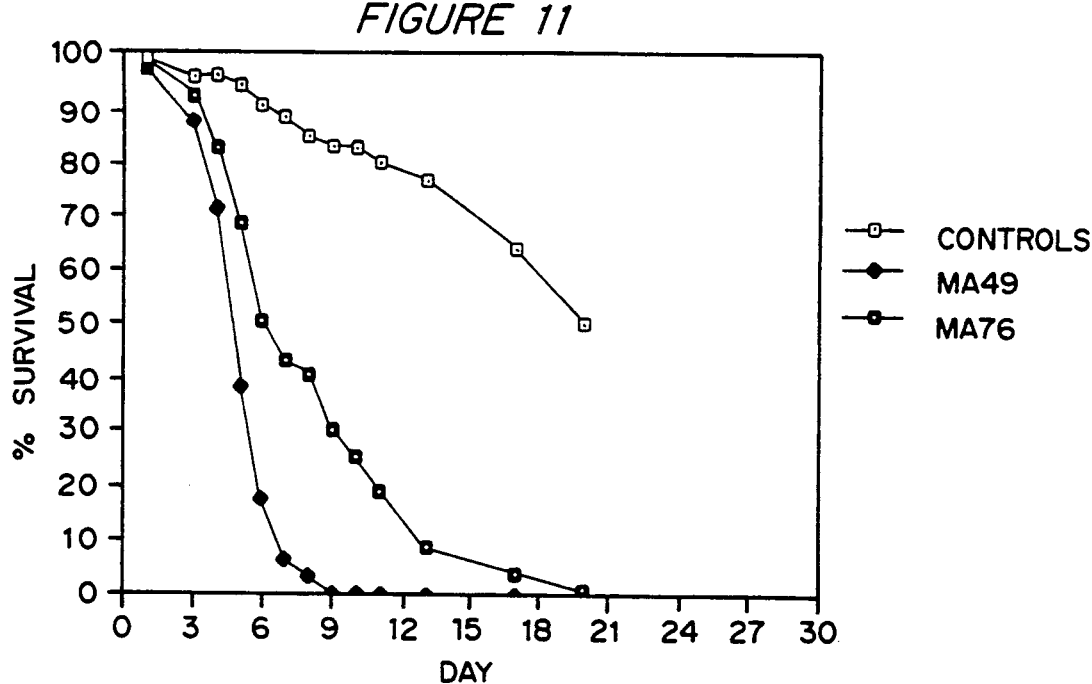
FIG. 11 is a graph of the mortality of *Fannia canicularis* (% survival) as a function of time after exposure (days) to a chamber containing *Metarhizium anisopliae,* strain ATCC MA 38249 (diamonds) or ATCC MA 62176 (empty squares), or chamber without fungus (dotted squares).
Figure 12:
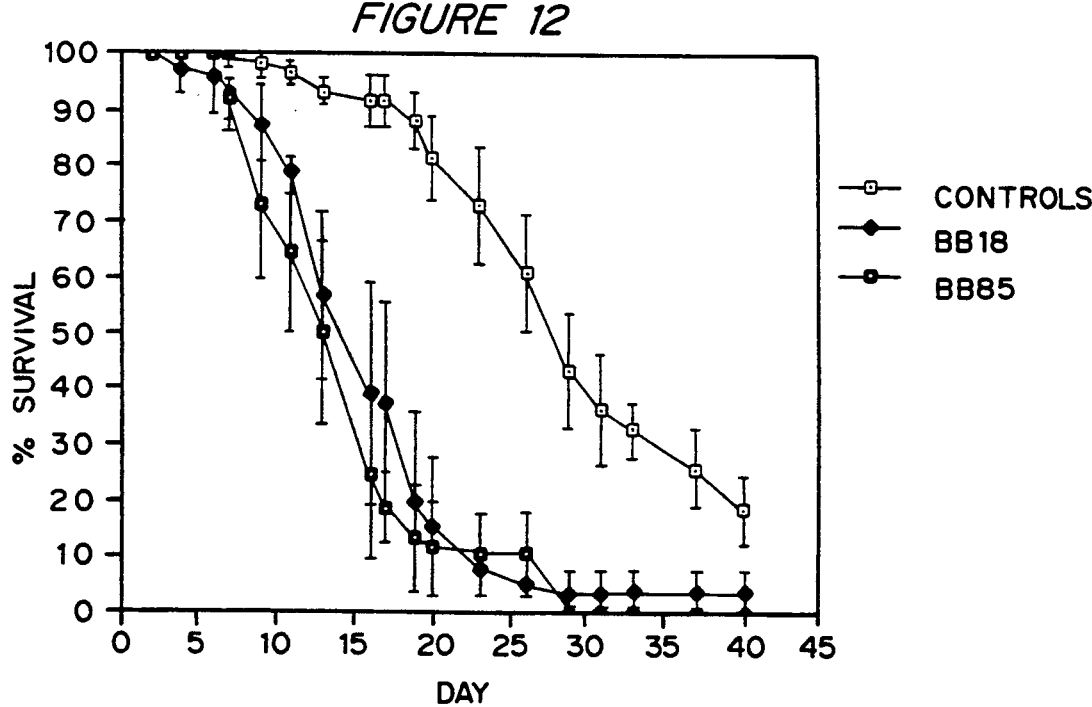
FIG. 12 is a graph of the mortality of *Fannia canicularis* (% survival) as a function of time after exposure (days) to a chamber containing *Beauveria bassiana,* strain ATCC 24318 (diamonds) or ATCC 48585 (empty squares), or a chamber without fungus (dotted squares).

After the adult flies emerged, mortality was recorded daily and plotted. Exposure of the adult flies to the chambers containing either of two strains of the fungi *Metarhizium anisopliae* or *Beauveria bassiana* resulted in a significant reduction in survival of adult house flies as compared to flies exposed to chambers without fungus, as shown by FIGS. 11 and 12, respectively. FIG. 11 summarizes the results of the study where flies were exposed to *M. anisopliae* strains 62176 and 38249. 80% of the flies were dead after only six days; almost 100% were dead by eight days following exposure to the fungus. FIG. 12 summarizes the results of the study where flies were exposed to *B. bassiana* strains 24318 and 48585. Essentially 100% of the flies were dead by four days following exposure to the fungus.

EXAMPLE 9

Control of *Musca domestica* in chicken coops using chambers containing *Metarhizium anisopliae*

The effectiveness of the chambers containing fungus for control of flies under field conditions, in contrast to laboratory conditions, was determined using two chicken coops 12'×21'×6', containing 20 chambers per coop, fresh chicken and cow manure, and 10,000 *M. domestica* flies. 100 flies were removed per coop four, eight, eleven and fifteen days after exposure to the chambers and reared in the laboratory to determine mortality. Fifteen paper sheets (8.5"×11") were placed in each coop for counting resting flies. Fifteen 3"×5" cards were placed in each coop for counting fecal and vomit spots as an indicator of the number of flies remaining after exposure to the chambers.

Figure 13:
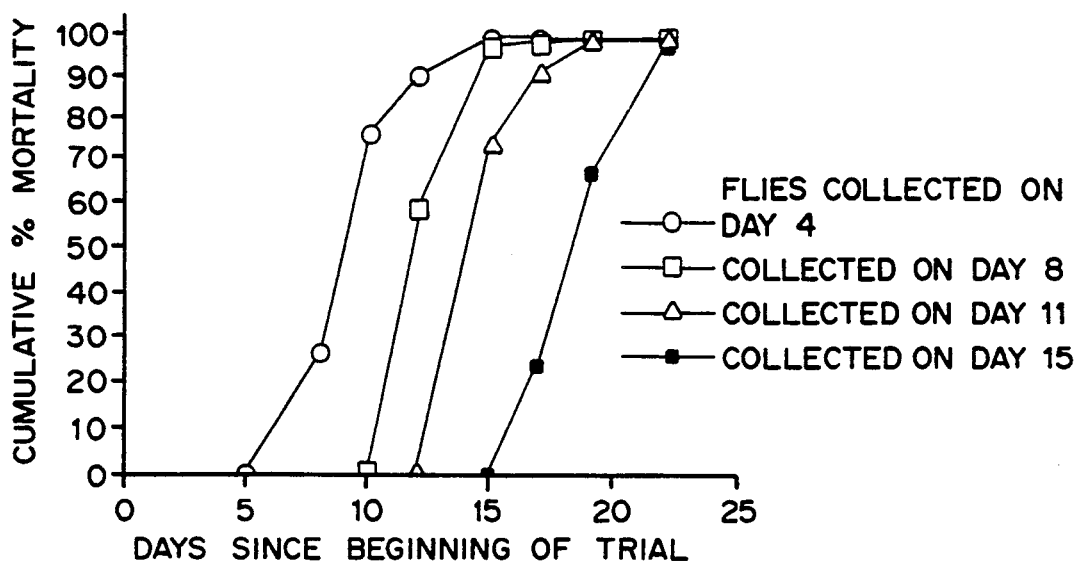
FIG. 13 is a graph of the cumulative percent mortality of *Musca domestica* (10,000 flies/coop) as a function of time after exposure (days) to infection chambers containing *Metarhizium anisopliae* in chicken coops: flies collected on day 4 (circles), flies collected on day 8 (empty squares), flies collected on day 11 (triangles), and flies collected on day 15 (reversed arrows).
Figure 14A:
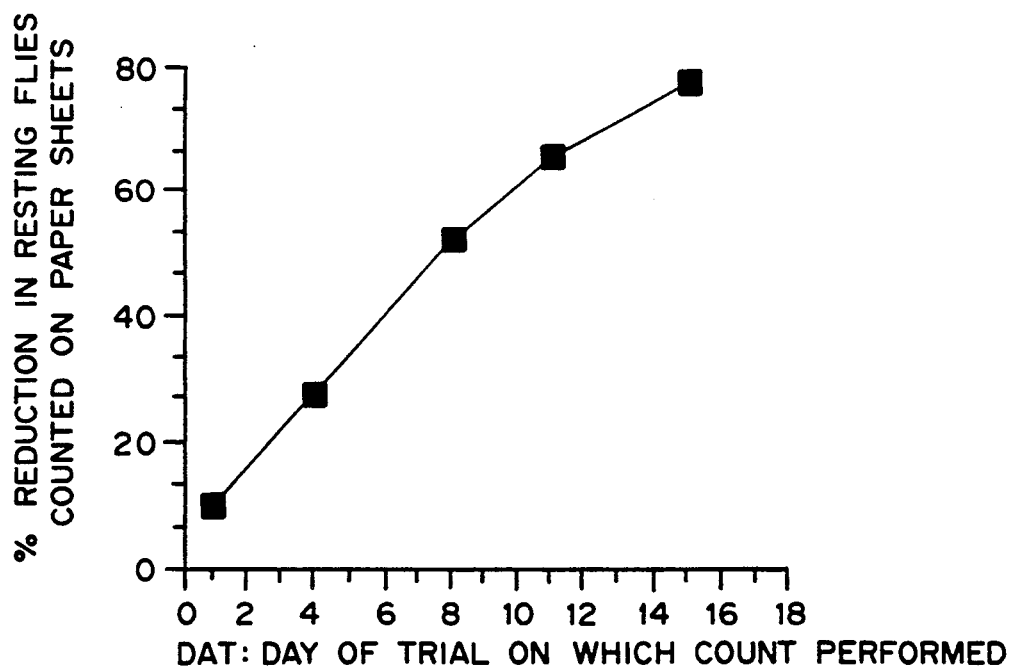
FIG. 14A is the percent reduction in resting flies of *M. domestica* (10,000 flies/coop) as a function of time after exposure (days) to infection chambers containing *M. anisopliae* in chicken coops.
Figure 14B:
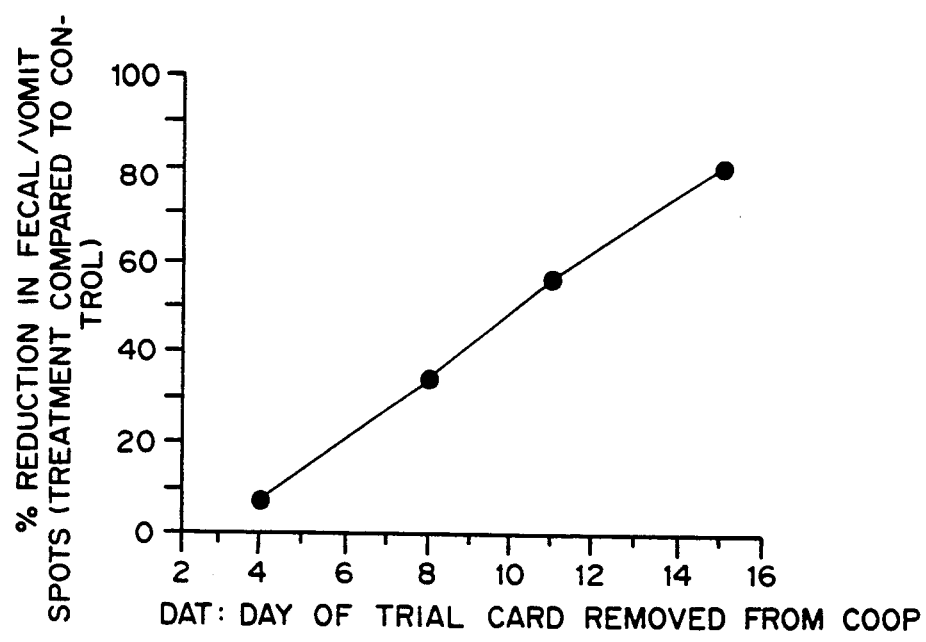
FIG. 14B is the percent reduction in fecal/vomit spots of *M. domestica* (10,000 flies/coop) as a function of time after exposure (days) to infection chambers containing *M. anisopliae* in chicken coops.

The results, graphically shown in FIG. 13, demonstrate that 100% mortality was achieved of all flies collected from the coops having chambers containing fungus. The results shown in FIG. 14A of the numbers of resting flies indicate a 78% reduction in flies by the fifteenth day. The results shown in FIG. 14B of the numbers of vomit and fecal spots indicate an 80% reduction in flies by the fifteenth day.

EXAMPLE 10

Control of *Diabrotica* using Chambers containing *Beauveria bassiana* 48585

Containers were constructed from round plastic boxes about 13" in diameter and 7" tall. Two holes about 3¾" in diameter were drilled in the side of each box. Footless stockings were glued to these holes, providing "sleeves" that allowed access to the inside of the box. When not in use, each sleeve was tied in a knot to prevent beetles from escaping. The boxes had lids which could be affixed securely during the experiment and removed afterwards. The bottoms of the boxes were lined with wet filter paper.

Pupae of *Diabrotica undecimpunctata* were held at 28° C. until adults emerged. Adults were collected and placed in the plastic boxes. 40 beetles were placed in each box.

Infection chambers were constructed from 60×15 mm Petri plates of fungus, *Beauveria bassiana* ATCC 48585, (empty Petri plates for the controls) and 5-oz. paper cups. The waxed paper cups were trimmed so that they fit over the Petri plates. Five rectangular openings, about 1½" long and 178" wide, were cut in the sides of each cup. Cups were inverted over the Petri plates and taped to them. Raisins were placed in the chambers as an attractant.

Chambers were hung inside boxes. Three boxes per treatment were used. Boxes were placed in an incubator at 27° C. and 76% relative humidity. There were no lights in this incubator.

A small dish of commercial diet (similar to the pollen substitute used by beekeepers), a few slices of raw zucchini or summer squash, and a 1-oz. cup of water were placed in each box. The cup was provided with a cotton wick from which the beetles could drink.

Boxes were serviced three times per week. Old food was removed, more water was pipetted onto the filter paper, and fresh food was added. Dead beetles were removed and counted. The study was terminated after two months (61 days).

Figure 15:
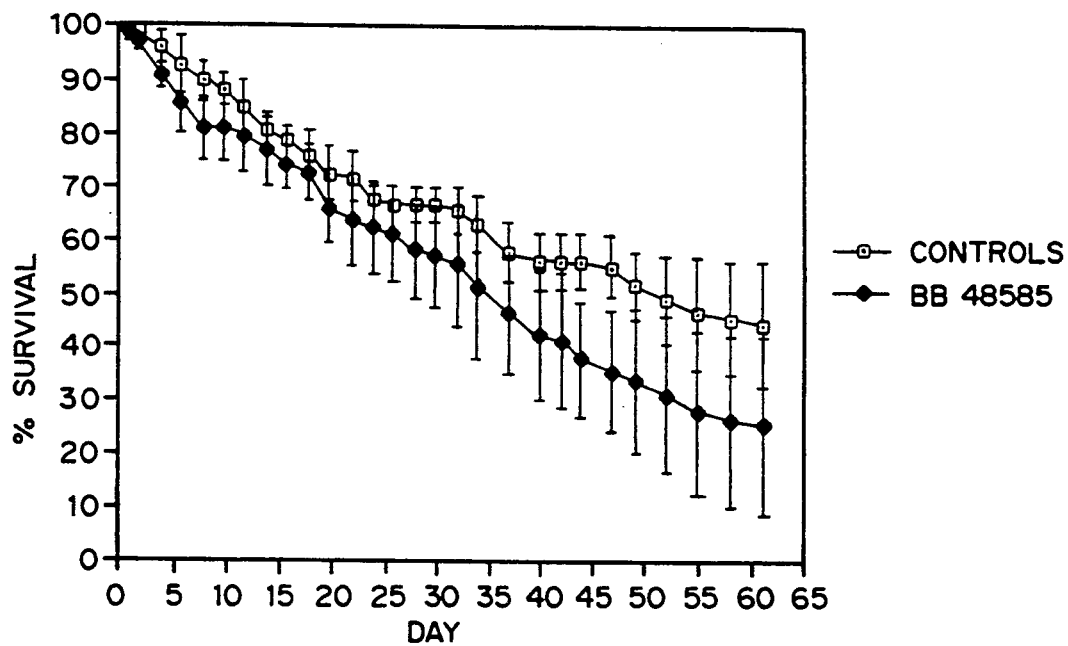
FIG. 15 is a graph of the percent survival over time (days) of *Diabrotica undecempunctata* adults exposed to chambers containing *Beauveria bassiana* 48585 (diamonds) compared with controls exposed to infection chambers not containing fungus (empty squares).

The results are shown in FIG. 15. The percent surviving adult beetles that were exposed to fungus was approximately one-half that of the control beetles not exposed to fungus.

Modifications and variations of the method and device for biological control of insects using entomopathogenic fungi in combination with an infection chamber will be obvious to those skilled in the art from the foregoing detailed description. Such modifications and variations are intended to come within the scope of the appended claims.

We claim:

1. A method for increasing the mortality rate of a targeted species of insects comprising providing a chamber attractive for the targeted insects,
   a) containing a live culture of a fungus that can be pathogenic for the targeted insects on a nutrient medium, the chamber protecting the fungal culture from the environment and concentrating a high number of a fungal inoculum in the chamber, and
   b) the geometry and shape of the chamber forcing the targeted insects attracted into the chamber into contact with an effective amount of the fungus to produce a lethal infection in the targeted insects.

2. The method of claim 1 wherein the insects are selected from the group consisting of roaches, flies, wasps, white flies, and the flying forms of beetles.

3. The method of claim 1 wherein the pathogenic fungus is selected from the group consisting of Metarhizium, Beauveria, Verticillium, Paecilomyces species and combinations thereof.

4. The method of claim 1 further comprising regulating moisture content of the chamber.

5. The method of claim 1 further providing a platform within the chamber, in close proximity to the fungal culture.

6. The method of claim 1 further comprising making the chamber attractive by making the chamber with a feature selected from the group consisting of color, shape, location, and combinations thereof attractive to the flying insects.

7. The method of claim 1 further comprising making the chamber attractive by adding a composition selected from the group consisting of chemical attractants, pheromones, and food.

8. The method of claim 1 further comprising a moisture retaining pad for maintaining humidity in the chamber.

* * * * *